United States Patent

Schödel et al.

[11] Patent Number: 5,804,689
[45] Date of Patent: Sep. 8, 1998

[54] PROCESS FOR RECOVERING ACETYLENE FROM HYDROCARBONS BY THERMAL CRACKING

[75] Inventors: Nicole Schödel, München; Eberhard Lassmann, Pullach; Holger Hackner, München, all of Germany

[73] Assignee: Linde Aktiengesellschaft, Wiesbaden, Germany

[21] Appl. No.: 593,624

[22] Filed: Jan. 30, 1996

[30] Foreign Application Priority Data

Jan. 30, 1995 [DE] Germany ............ 195 02 857.0

[51] Int. Cl.[6] .................................................. C07C 11/24
[52] U.S. Cl. ..................... 585/539; 585/540; 585/709
[58] Field of Search .................... 585/539, 709, 585/540

[56] References Cited

U.S. PATENT DOCUMENTS

| | | | |
|---|---|---|---|
| 2,974,180 | 3/1961 | Koble et al. | 585/539 |
| 3,161,695 | 12/1964 | Goffinet, Jr. | 585/539 |
| 3,635,038 | 1/1972 | Nagel et al. | 585/539 |
| 3,644,555 | 2/1972 | Nagy et al. | 585/539 |
| 3,660,016 | 5/1972 | John et al. | 423/226 |
| 3,686,344 | 8/1972 | Brunner | 585/540 |
| 4,136,015 | 1/1979 | Kamm et al. | 585/634 |
| 4,367,363 | 1/1983 | Katz et al. | 585/539 |
| 4,570,028 | 2/1986 | Voelz et al. | 585/540 |
| 4,575,383 | 3/1986 | Lowther et al. | 585/540 |

*Primary Examiner*—Margaret Medley
*Attorney, Agent, or Firm*—Millen, White, Zelano, & Branigan, P.C.

[57] ABSTRACT

For recovering acetylene from hydrocarbons, the hydrocarbons are thermally cracked in the presence of $CO_2$ as a diluent gas. Suitable for thermal cracking for acetylene generation is a ratio, by weight, of $CO_2$ to hydrocarbon, of between 3:1 and 1:3, and preferably between 2:1 and 1:2. It is preferred for the $CO_2$ to be mixed with the hydrocarbons before thermal cracking which is thereafter conducted at average reaction temperatures of between 800° and 1200° C., preferably between 900° and 1100° C. An average residence time of between 5 and 500 milliseconds (ms) of the hydrocarbons during thermal cracking has proven to be effective. As the hydrocarbon feedstock for the thermal cracking, basically $C_{2+}$ alkanes, especially ethane, propane and/or butane, can be used advantageously. After the cracked gas is cooled, higher alkynes are removed from the cracked gas, then the acetylene is separated preferably by scrubbing with an absorption agent selective for acetylene. Recycle streams of hydrocarbons and/or $CO_2$ for the thermal cracking can contribute to savings and more efficient use of the feedstock.

18 Claims, 6 Drawing Sheets

PROCESS FOR RECOVERING ACETYLENE FROM HYDROCARBONS BY THERMAL CRACKING

FIELD OF THE INVENTION

The invention relates to a process for recovering acetylene from hydrocarbons by means of thermal cracking of hydrocarbons.

BACKGROUND OF THE INVENTION

The thermal processes for the production or recovery of acetylene are based on the uncatalyzed pyrolysis of hydrocarbons. Numerous processes have been developed for industrial acetylene recovery by means of thermal cracking. These processes can be divided basically into three process types, in which mainly the feedstocks used, the composition of the effluent, and especially the type of heat transfer used to obtain the temperatures necessary for the cracking reaction determine each type.

The first process type is based on the electrothermal cracking of the hydrocarbons, with heating generally being accomplished with an electric arc which process is therefore also referred to as the electric arc process. Electrothermal cracking is considered an allothermal process with direct heat transfer.

In a second process type, external heat is transferred indirectly. This process is also allothermal, with indirect heat transfer via a heat transfer medium. For this purpose, the use of regenerative-furnace systems using a refractory mass has been suggested, as well as the possibility of direct—fired tubes containing hydrocarbons diluted with steam.

The cracking of hydrocarbons for recovering acetylene is carried out in the third process type by partial combustion of the hydrocarbon feedstock. This process is auto-thermal, and the heat from the partial combustion of the hydrocarbon feedstock is used for endothermal cracking of the hydrocarbon radical.

The above-named process types are described in, for example,

"Industrielle Organische Chemie [Industrial Organic Chemistry]," K. Weissermel and H. -J. Arpe, Fourth Edition (1994), page 99 ff, "Ullman's Encyclopedia of Industrial Chemistry," Fifth Edition (1985), Volume A1, page 97 ff, and "Encyclopedia of Chemical Technology," Kirk and Othmer, Third Edition (1978), Volume 1, page 211 ff and Concise Encyclopedia of Chemical Technology", Kirk-Othmer, 1985, pages 16, 17.

The previously known processes according to the second process type have not been proven to be effective. The regenerative processes have the drawback of requiring an extremely large amount of refractory mass to compensate for frequent temperature variations. In addition, a very substantial amount of carbon black (soot) is formed.

As for the technical processes that are conventionally used for the production of acetylene, they require considerable energy because of the required very high temperatures and the low level of achievable energy efficiency. In these processes according to the prior art, large amounts of coke accumulate—between 5 and 60 kg of coke per 100 kg of acetylene—which represent an additional loss. Another problem of the known processes is that high selectivities of acetylene and ethylene are not achieved. These disadvantages apply in principle to both processes used industrially according to the first and third process types. It turns out, however, that the weighing of the individual drawbacks is different for the different process types. Thus, in the process based on electrothermal cracking, on the one hand, the energy consumption, of about 1000 to 1200 kWh per 100 kg of acetylene, is extraordinarily high, and on the other hand, about 10 to 60 kg, typically about 30 kg, of coke per 100 kg of acetylene, accumulates. Moreover, the electric arc process requires very costly equipment. An advantage of the electric arc process, on the other hand, is that high selectivities for acetylene and ethylene, at 56–78% by weight of the hydrocarbon feedstock, can be achieved, with weight ratios of acetylene to ethylene of 1:1 to 2:1.

In the process using partial combustion, energy consumption and coke accumulation are lower, but on the down side, the selectivities for acetylene and ethylene are also lower, only 20 to 50% by weight of hydrocarbon feedstock being achieved with this process. For selectivities of about 50% by weight, the weight ratio of acetylene to ethylene is between 1:2 and 3:1.

SUMMARY OF THE INVENTION

An object of this invention is to provide a thermal cracking process that is relatively highly energy-efficient compared to known processes and which also provides relatively high selectivities for acetylene and ethylene. Another object is to provide a process wherein the equipment cost is comparatively low.

Still another object is to provide a process which mitigates the formation of coke. (In the context of this invention, coke is meant to include carbon black and soot as well.)

A still further object is to provide a process permitting relatively flexible control of the product composition of ethylene and acetylene.

Upon further study of the specification and appended claims, further objects and advantages of this invention will become apparent to those skilled in the art.

To attain these objects the thermal cracking of hydrocarbons is carried out in the presence of $CO_2$.

Thermal cracking according to the invention is carried out in a reactor with reactor tubes. In this case, the heat is transferred indirectly. The process according to the invention is essentially allothermal with indirect heat transfer and therefore falls mainly into the second process type of thermal process for acetylene recovery.

Surprisingly, it has been found in the process according to the invention that, by the addition of $CO_2$, the thermal cracking of the hydrocarbons for the production of acetylene can be carried out at lower temperatures than was assumed heretofore. At the same time, the formation of coke in the process according to the invention can be prevented or at least effectively reduced. This means that carbonizing of the reactor tubes and consequent plugging of the reactor in the process according to the invention do not occur or occur only to an insignificant extent.

A ratio, by weight, of $CO_2$ to the hydrocarbons in thermal cracking, of preferably about 3:1 to 1:3, and especially 2:1 to 1:2, has been found to be especially advantageous. When $CO_2$ is added to the hydrocarbons, in the specified ranges, virtually no formation of coke or very slight coke formation occurs. The accumulation of coke was under 5 kg per 100 kg of acetylene produced in experiments using the process according to the invention. The addition of $CO_2$ to the hydrocarbons can be varied within the above-mentioned ranges in the process according to the invention, and the product composition of ethylene and acetylene can be varied on the basis of the hydrocarbon feedstock and the reaction temperature. Conversely, $CO_2$:hydrocarbon ratios that are too high in the thermal cleavage step result in hydrocarbon losses and in the formation of CO and $H_2$. $CO_2$:hydrocarbon ratios that are too low result in an excessive and undesirable amount of coke.

Advantageously, $CO_2$ is mixed with the hydrocarbons to be cracked before thermal cracking. This ensures especially effective prevention of coke formation.

Thermal cracking is carried out according to the invention at average reaction temperatures of preferably about 800°–1200° C., and especially 900°–1100° C. These temperatures are, on average, considerably below the reaction temperatures of the known processes and contribute essentially to the high energy-efficiency of the process according to the invention.

Advantageously, the average residence time of the hydrocarbons in the case of thermal cracking, which involves the heating time and cracking time within the range of reaction temperatures until the cracked gas is cooled, is preferably about 5–500 ms (milliseconds), especially 30–200 ms, and especially preferably 50–150 ms. The feedstock is generally preheated to a temperature of about 400° to 650° C., the specific temperature being dependent on the hydrocarbon feedstock, before being added to the reactor. In this case, the final temperature in the preheating phase is selected so that no noticeable cracking of the hydrocarbons commences. In the reactor, the heating of the hydrocarbons to the reaction temperatures is first accomplished during the heating time, and increasingly the cracking of the hydrocarbon starts to occur. The estimated time for heating the more or less preheated gas from 400°–650° to 800°–1200° C. will be approximately one third or 20–40% of the total time necessary for heating and cracking. In the range of reaction temperatures, the desired cracking into acetylene then ultimately proceeds to an appreciable extent. By the selection of the average residence time, especially the cracking time, the product composition of ethylene and acetylene can be varied. For example, an increased cracking time results in a decreased $C_2H_4$:$C_2H_2$ ratio and in an increased carbon content.

As the feedstock, all feedstocks which contain hydrocarbons that are known to be useful for the thermal cracking of hydrocarbons to recover acetylene are used in the process according to the invention; however, $C_{2+}$ alkanes, especially ethane, propane and/or butane, are preferably used as hydrocarbons for thermal cracking. Owing to their relatively low thermodynamic temperatures, i.e., the minimum temperature for the formation of acetylene—as a function of the pressure and the composition of the gas, these alkanes are especially suitable as feedstock for reaction to acetylene for the process according to the invention.

In a comprehensive embodiment embracing the process according to the invention, higher alkynes are at least partially, if not essentially, completely removed from the cracked gas after the cracked gas is cooled, and then acetylene is at least partially, if not essentially, completely separated from the remaining cracked gas, especially by scrubbing the gas with an absorption agent that is selective for acetylene.

As a selective absorption agent for the separation of acetylene from the cracked gas, any known selective absorption agent can be used. Particular suitable absorption agents include but are not limited to: dimethylformamide (DMF), N-methylpyrrolidone (NMP), acetone, methanol, γ-butyrolactone, $NH_3$ or mixtures thereof.

The cracked gas that is liberated at least partially of acetylene and higher alkynes can optionally be recycled for thermal cracking after a purge-stream is separated. Greater use of the hydrocarbon feedstock is thus achieved by this recycle stream. The amount the recycle stream is purged will be dictated by composition of the feed gas and the equipment size.

According to the invention, $CO_2$ that is contained in cracked gas can be separated and recycled for thermal cracking. The amount of external $CO_2$ added to the process can come from, for example, flue gas or acidic natural gas. Advantageously, $CO_2$ is removed from the cracked gas by regenerative scrubbing with an absorption agent that is selective for $CO_2$. All known absorption agents that are selective for $CO_2$ can be used, particularly suitable absorption agents including but not limited to amine- (e.g., ethanolamine-), $NH_3$— and/or potash-containing (e.g., $K_2CO_3$) absorption agents.

In another embodiment of the invention, olefins, especially ethylene, are separated from cracked gas that is liberated of at least partially, if not essentially completely of acetylene and of alkynes and optionally $CO_2$. The separation of the olefins can be carried out, for example, by scrubbing with a selective absorption agent, by a membrane-separating process, by an adsorption process, or by a cryogenic separating process, e.g., rectification.

In another embodiment of the invention, the residual cracked gas that is liberated at least partially, if not essentially completely, of acetylene and of alkynes and optionally $CO_2$ and/or olefins, can be combusted at least partially by air and/or oxygen, and the heat that is recovered in this case can be used at least partially for heating the reactor for thermal cracking by indirect or direct heat transfer.

In the case of all processes of thermal cracking of hydrocarbons for recovering acetylene, the cracked gas must be cooled quickly to prevent the acetylene from decomposing into soot and hydrogen after equilibrium is established. The quick cooling of the reaction gas is generally carried out by injecting water or quenching oil into a quenching condenser immediately after thermal cracking. In the process according to the invention, quenching with oil, for example, pyrolysis oil, with concomitant energy recovery is preferred. In such a quench cooling step, coke, oil, especially heavy oil, and/or an aromatic compound-containing gasoline are separated from the cracked gas. According to the invention, these hydrocarbons that are separated from the cracked gas by quench cooling can be combusted at least partially with the addition of air and/or oxygen, and the heat that is recovered can be used at least partially by indirect or direct heat transfer for heating the thermal cracking reactor.

By using heat recovered in the combustion of secondary process streams, the demand for external heat in the process according to the invention can be further reduced. Thus, the energy efficiency of the process can be additionally increased. The process according to the invention is thus operated at least partially autothermally in this embodiment.

The combustion of secondary processing streams results in a waste gas that contains $CO_2$. This $CO_2$ contained in the combustion waste gas can be recycled at least partially into the thermal cracking step as a diluent gas.

In a further development of the invention, in addition to $CO_2$, inert gases are present in or added to the feed gas for thermal cracking. These can be, for example, nitrogen or a mixture of nitrogen and argon. While nitrogen, without $CO_2$, in the feed gas at temperatures that are suitable for the production of acetylene results in rapid carbonization of the reactor tubes, carbonization can be avoided to a very large extent when $N_2$ together with $CO_2$ is present in the feed gas. The inert gases are not intended to replace $CO_2$ in accordance with the invention. However, they can indirectly affect the process by changing the partial pressure. For example, the lower the nitrogen content the lower its partial pressure and the higher the acetylene content of the acetylene/ ethylene product. However, since inert gases will have to be separated from the product, it is preferred not to have inert gases in the feed gas.

The use of steam as a diluent, on the other hand results in undesirable losses of acetylene owing to the formation of CO and $H_2$. Therefore, according to another aspect of the invention, steam is not employed as a diluent gas for thermal cracking. As a result, the entire process is anhydrous, which has an advantageous effect on the scrubbing step since removal of water from the absorption agent is no longer necessary.

The following table of test results clearly shows advantages of the process according to the invention conducted with a weight ratio of $CO_2$ to hydrocarbon of between 2:1 and 1:2 compared to a process according to the prior art.

| Parameters | Prior Art | Invention |
| --- | --- | --- |
| Average reaction temperature | about 1200–1500° C. | about 900–1100° C. |
| Residence time | about 2–30 ms[1] | about 50–150 ms[2] |
| Conversion relative to the hydrocarbon feedstock | about 20–100% | about 90–100% |
| Yield of acetylene and ethylene | about 10–55 mol % | about 50–75 mol % |
| Ratio of $C_2H_4/C_2H_2$ | about 3:1 to 0.1:1 by weight | about 7:1 to 0.4:1 by weight |

[1] without heating time
[2] including heating time

The test results that are presented in the table confirm the significant increase in the yield of acetylene and ethylene in the process according to the invention at comparatively lower reaction temperatures. In addition, the product composition of ethylene and acetylene can be varied within a considerable range with the process according to the invention by properly selecting the operating parameters. The lower reaction temperatures also result in lower expenditures for energy, equipment and maintenance.

BRIEF DESCRIPTION OF DRAWINGS

The invention as well as additional details of the invention are explained in more detail below based on the preferred embodiments depicted in the drawings, wherein.

DETAILED DESCRIPTION OF FIGURES

In FIGS. 1 to 6, the same or equivalent process stages or process streams are given identical reference numbers. Broken lines in the figures identify optional process stages and optional connections.

Figure 1:
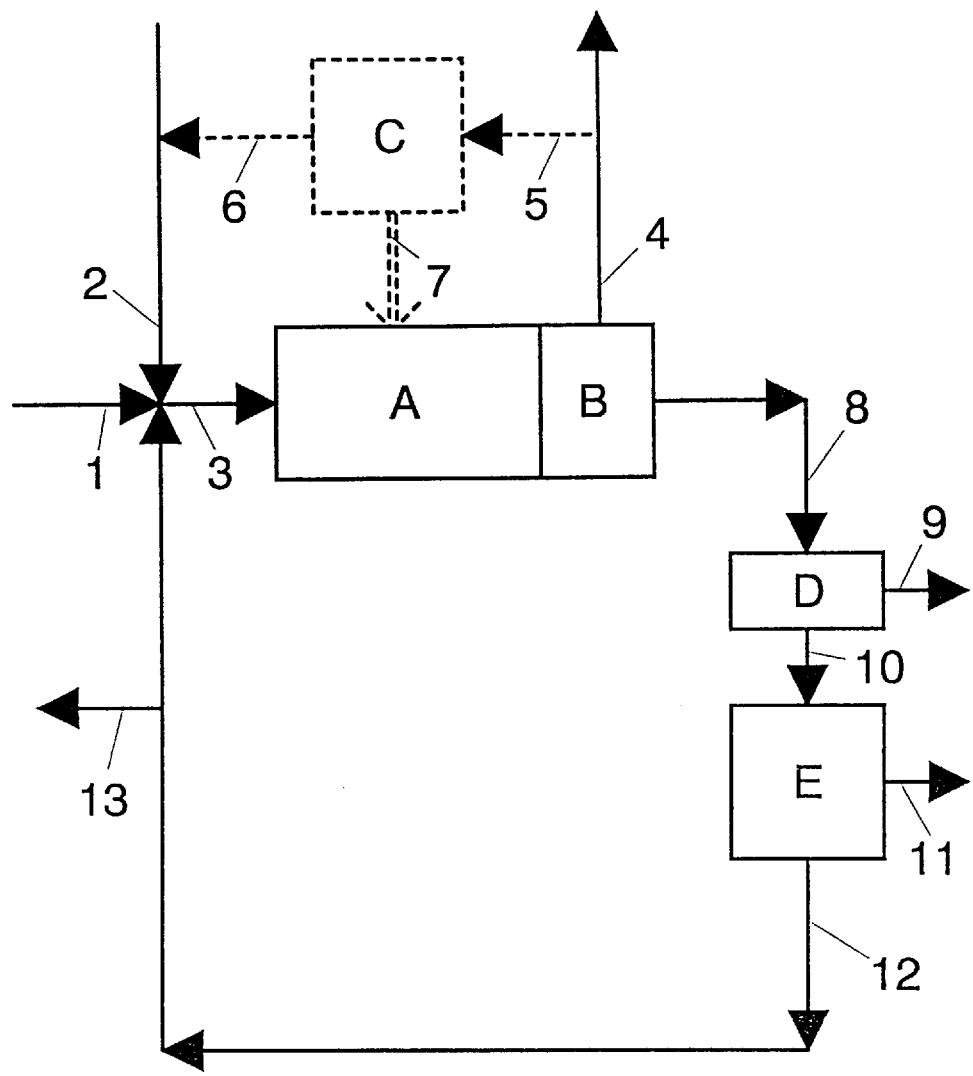
FIG. 1: is a schematic flowsheet of a thermal cracking process with residual gas recycle and acetylene recovery but without separation of olefins.

In FIG. 1, a feedstock stream containing the hydrocarbons to be cracked, for example, a non-combusted gas comprising alkanes (e.g., ethane, propane and/or butane) in line 1, is diluted with $CO_2$ from line 2. In addition, a hydrocarbon-containing recycle gas from line 12 is mixed therewith. The gas mixture is sent to thermal cracking stage A via line 3. After the cracking is completed, the cracked gas is quickly cooled by quench cooler B with, for example, pyrolysis oil. In this case, for example, coke, heavy oil, and aromatic gasoline are separated via line 4. The quick cooling of the cracked gases can be done in several sequential stages, and at least the first stage comprises quench cooler B. The hydrocarbons are separated from the cracked gas in quench cooler B can optionally be combusted at least partially via line 5 in stage C with the addition of air and/or oxygen. The $CO_2$ that is contained in the combustion gas from stage C can be passed via line 6, to line 2 where it is used as the $CO_2$ diluent to be mixed with the feedstock. The resultant heat from combustion stage C, as indicated by double arrow 7, can be transferred to thermal cracking stage A. The cracked gas, which is cooled to temperatures at least as low as about 200° C. in line 8, is sent to prescrubbing stage D. Higher alkynes are separated from the cracked gas via line 9 in the prescrubbing stage D. In the subsequent acetylene scrubbing stage E with internal desorption and regeneration stages, acetylene is separated from the cracked gas and, after fine purification, is recovered as product-acetylene via line 11. The residual cracked gas is drawn off from the acetylene scrubbing stage via line 12 and recycled towards the hydrocarbon feedstock in line 1. After a purge stream 13 is separated from the recycle gas, the remainder is mixed with the feedstock.

Figure 2:
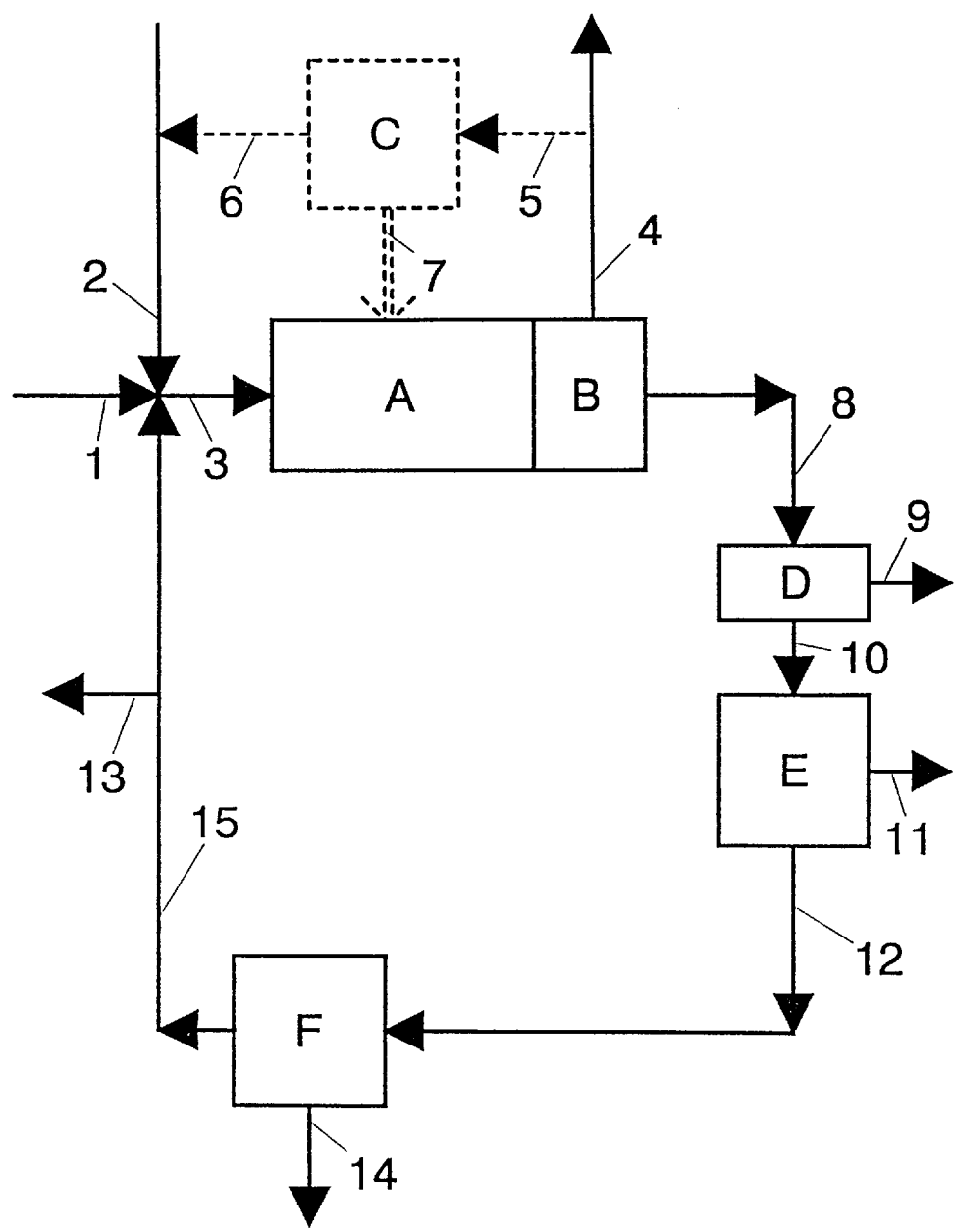
FIG. 2: is a schematic flowsheet similar to FIG. 1 but with both acetylene and olefin recovery.

In the process according to FIG. 2, unlike the process according to FIG. 1, the residual cracked gas that is drawn off from acetylene scrubbing stage E is fed to line 12 of an olefin separation F, preferably, an olefin scrubbing stage using regenerable chemical or physical scrubbing agents, although an economic analysis of a particular system might demonstrate that an adsorption system would be a better alternative. The olefins, basically ethylene, are drawn off via line 14 from olefin separation F. The residual gas from olefin separation F in line 15 is mixed in with the hydrocarbon feedstock in line 1 after a purge stream 13 is removed.

Figure 3:
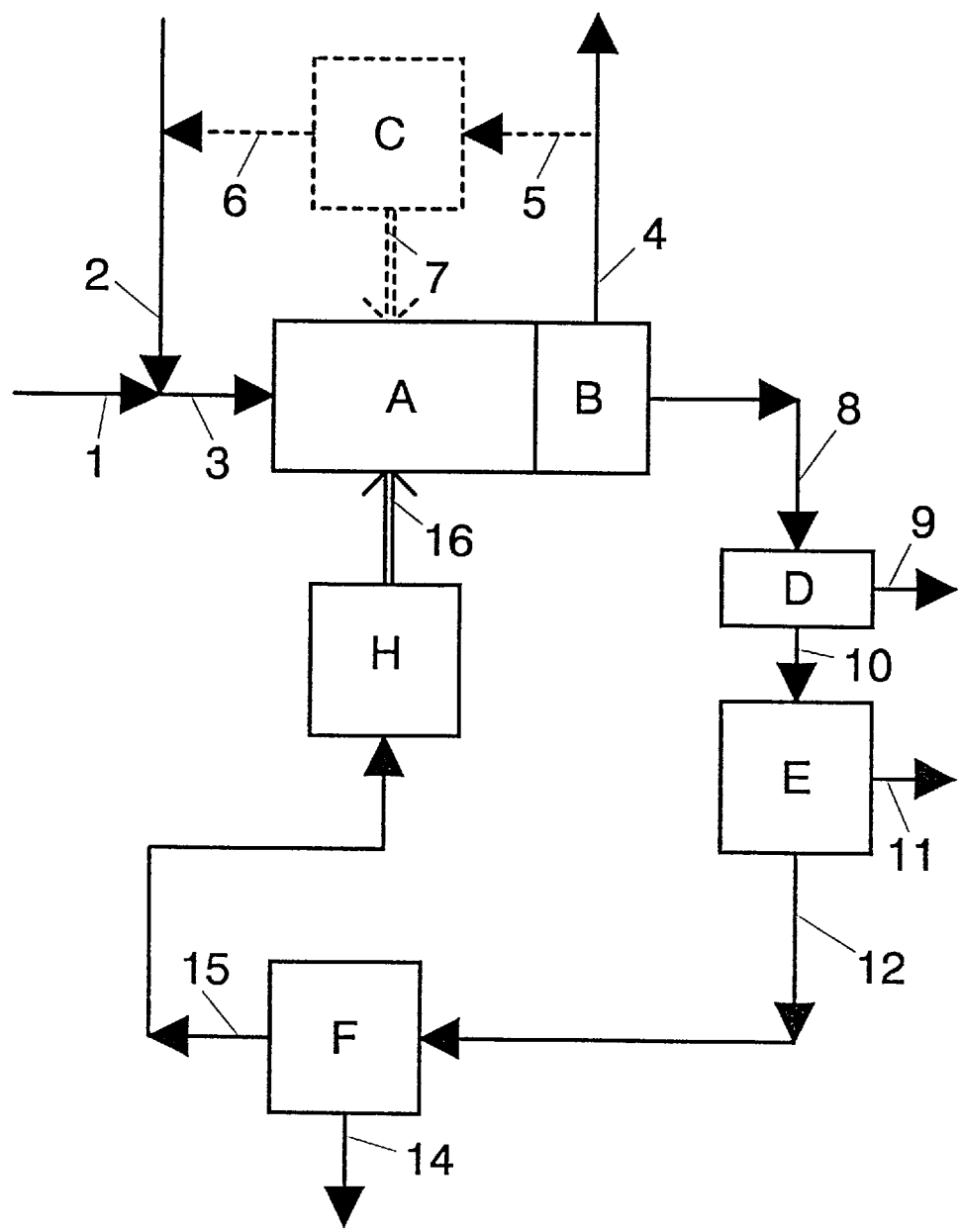
FIG. 3: is a schematic flowsheet of thermal cracking with acetylene and olefin recovery without residual gas recycle stream.

Unlike the process depicted in FIG. 2, in the process shown in FIG. 3 the residual gas from olefin separation F in line 15 is directed to a residual gas combustion stage H with oxygen and/or air supply. The heat that is produced therein is transferred from residual gas combustion H, as indicated by double arrow 16, to thermal cracking A.

Figure 4:
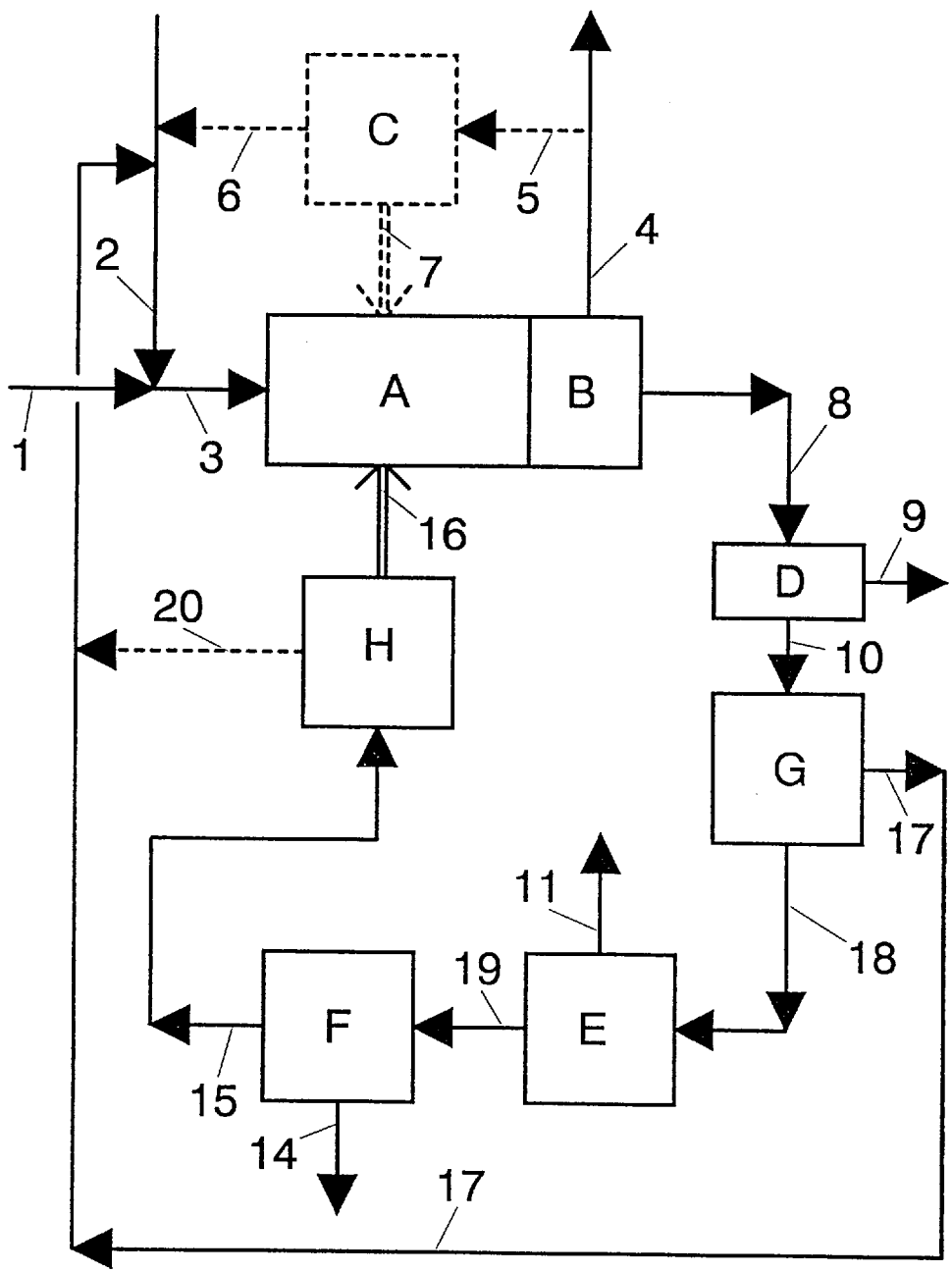
FIG. 4: is a schematic flowsheet of a thermal cracking process with $CO_2$ recycling and acetylene and olefin recovery.

The process depicted in FIG. 4 differs from the process according to FIG. 3 in that between the presumably stage E to remove alkynes and the acetylene scrubbing stage E, a regenerative scrubbing stage G for selective removal of $CO_2$ is provided. The $CO_2$ that is separated from selective $CO_2$ scrubbing stage G is mixed via line 17 in with the $CO_2$ in line 2. In addition, the $CO_2$ that accumulates during the residual gas combustion in stage H can be mixed via line 20 in with the $CO_2$ recycle stream in line 17.

Figure 5:
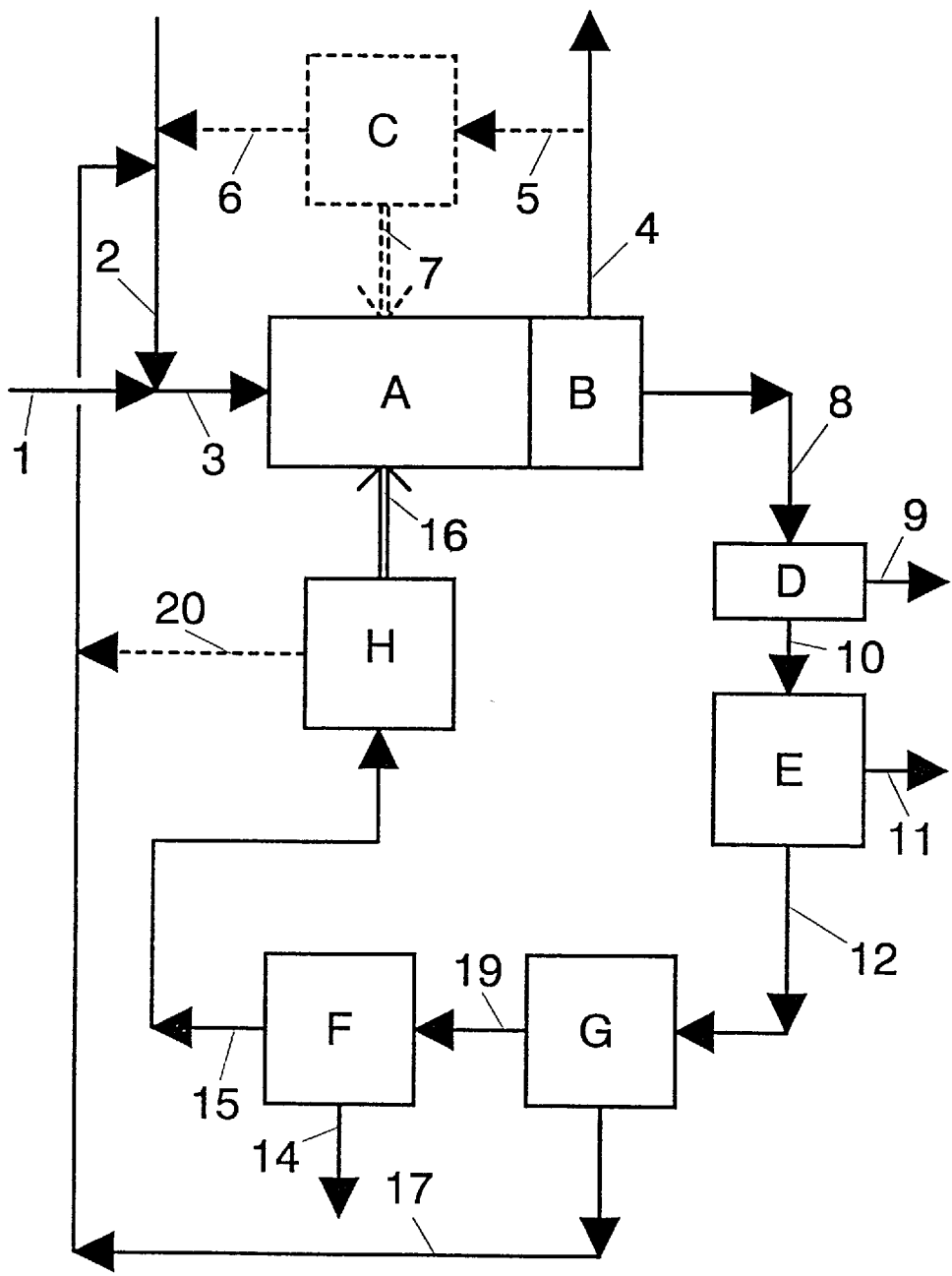
FIG. 5: is a schematic flowsheet of a thermal cracking process with acetylene recovery, $CO_2$ recycling and olefin recovery.

In the process illustrated in FIG. 5, unlike the process according to FIG. 4, the sequence of acetylene scrubbing stage E and the $CO_2$ scrubbing stage G is reversed. In the process according to FIG. 5, the selective $CO_2$ scrubbing stage G is downstream from acetylene scrubbing stage E.

Figure 6:
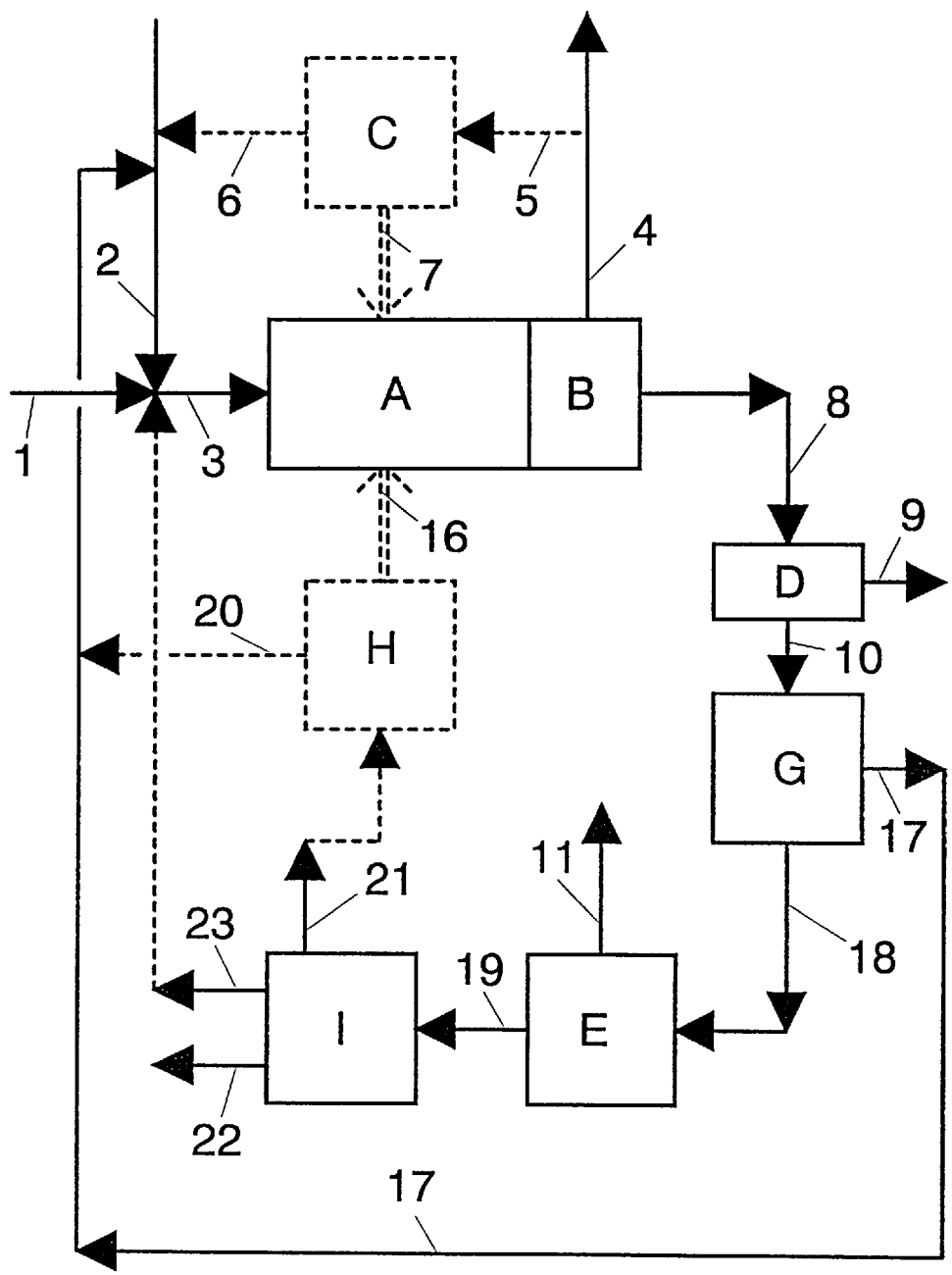
FIG. 6: is a schematic flowsheet of a thermal cracking process with $CO_2$ recycling, acetylene recovery and individual component recovery of hydrocarbons in the residual gas.

The process shown in FIG. 6 is distinguished from the process depicted in FIG. 4 by a comprehensive residual gas workup stage I, which comprises, for example, a low-temperature separation system instead of the simple olefin separation F of FIG. 4. In the residual gas workup stage I, olefins, especially ethylene, are drawn off via line 22. $CH_4$, CO and $H_2$ on the other hand are drawn off via line 21 from residual gas workup stage I and can be directed to the residual gas combustion stage H. In the residual gas workup stage I, alkanes are also ultimately recovered via line 23, which alkanes can be mixed in with the hydrocarbon feedstock in line 1. Conventional processes used in ethylene plants for example, are employed to separate the olefins, $CH_4$, CO and $H_2$, with low temperature separation processes being preferred. The process according to FIG. 6 can be further modified by virtue of the fact that, as in the process of FIG. 4, the selective $CO_2$ scrubbing stage G can be repositioned downstream from acetylene wash E.

According to the Figures, there is not separate preheating stage shown because it is dispensable. There may exist an external preheating stage, e.g., in the scope of a heat recovery, or the heat of reaction accumulating in the reactor can be used, or a combination of both.

The entire disclosure of all applications, patents and publications, cited above and below, and of corresponding German application P 19502857.0, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for producing acetylene from hydrocarbons by thermal cracking of hydrocarbons, the improvement comprising conducting the thermal cracking of the hydrocarbons in the presence of $CO_2$ as a diluting gas by mixing the $CO_2$ with the hydrocarbons such that the weight ratio of $CO_2$ to hydrocarbons is between 2:1 and 1:2 before conducting the thermal cracking wherein the thermal cracking includes a heating time with heat being provided by indirect heat transfer and a cracking time at a reaction temperature of between 900° and 1100° C. and the average residence time, including heating time and cracking time, is between 50 and 150 ms.

2. The process of claim 1, wherein the hydrocarbons contain $C_{2+}$ alkanes.

3. The process of claim 2, wherein the hydrocarbons contain ethane, propane, and/or butane.

4. The process of claim 1, further comprising cooling the resultant cracked gas, removing higher alkynes from the cracked gas and then separating acetylene by scrubbing with an absorption agent that is selective for acetylene.

5. The process of claim 4, wherein the absorption agent is selected from the group consisting of dimethylformamide (DMF), N-methylpyrrolidone (NMP), acetone, methanol, γ-butyrolactone, $NH_3$ and mixtures thereof.

6. The process of claim 1, further comprising liberating the cracked gas of at least acetylene and essentially all higher alkynes, separating a purge stream and recycling the remaining gas for thermal cracking.

7. The process of claim 1, further comprising separating and recycling $CO_2$ contained in the resultant cracked gas for thermal cracking.

8. The process of claim 7, wherein the $CO_2$ is separated from the cracked gas by regenerative washing with an absorption agent selective for $CO_2$.

9. The process of claim 8, wherein the absorption agent is an amine-, $NH_3$—, and/or potash-containing agent.

10. The process of claim 1, further comprising liberating the resultant cracked gas of acetylene, essentially of all alkynes and optionally of $CO_2$, and then separating olefins therefrom.

11. The process of claim 10, wherein the separation of olefins is carried out by scrubbing with a selective absorption agent, by a membrane separating process, by an adsorption process, or by a low-temperature separating process.

12. The process of claim 1, further comprising liberating the resultant cracked gas of at least acetylene, essentially all alkynes and optionally of $CO_2$ and/or olefins, combusting it at least partially with the addition of air and/or oxygen, recovering the heat for heating the hydrocarbons by indirect heat transfer.

13. A process according to claim 1, further comprising quenching the cracked gases from the thermal cracking of hydrocarbons, combusting a fraction thereof with the addition of air and/or oxygen, and using the resultant heat at least partially for heating hydrocarbons in the thermal cracking by indirect heat transfer.

14. The process of claim 13, wherein the combusted fraction contains coke, heavy oil, and/or aromatic gasoline.

15. The process of claim 12, wherein $CO_2$ contained in the waste gas of the combustion is recycled at least partially as a diluting gas for the thermal cracking.

16. The process of claim 1, wherein the thermal cracking is conducted in the absence of steam.

17. The process of claim 1, wherein the thermal cracking is conducted in the presence of an inert gas, in addition to $CO_2$.

18. The process of claim 17, wherein the inert gas comprises $N_2$.

* * * * *